US00PP35087P2

(12) United States Plant Patent
Schwartz et al.

(10) Patent No.: US PP35,087 P2
(45) Date of Patent: Apr. 4, 2023

(54) BERMUDAGRASS NAMED '12-TG-101'

(50) Latin Name: ***Cynodon transvaalensis* x *Cynodon dactylon***
Varietal Denomination: 12-TG-101

(71) Applicant: University of Georgia Research Foundation, Inc., Athens, GA (US)

(72) Inventors: Brian Schwartz, Tifton, GA (US); Wayne W. Hanna, Chula, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/743,130

(22) Filed: May 12, 2022

(51) Int. Cl.
*A01H 5/12* (2018.01)
*A01H 6/46* (2018.01)

(52) U.S. Cl.
USPC ..... Plt./389

(58) Field of Classification Search
USPC ..... Plt./389, 388
CPC ... A01H 5/12; A01H 5/00; A01H 5/02; A01H 6/46; A01H 6/4612
See application file for complete search history.

(56) References Cited

U.S. PATENT DOCUMENTS

PP31,139 P3 * 11/2019 Lingle ..... A01H 6/4612 Plt./389

* cited by examiner

*Primary Examiner* — June Hwu
(74) *Attorney, Agent, or Firm* — Thomas Horstemeyer, LLP

(57) ABSTRACT

A new and distinct cultivar of Bermudagrass hybrid *Cynodon transvaalensis* x *Cynodon dactylon* named '12-TG-101' is provided. The new and distinct upright variety is characterized by a combination of superior turfgrass uniformity, very dark green leaf color, and high putting green speeds. The asexually reproduced triploid variety is reliably propagated vegetatively.

4 Drawing Sheets

DESCRIPTION

Latin name: Bermudagrass '12-TG-101' is an inter-specific hybrid of the genus *Cynodon* and species *Cynodon transvaalensis* x *Cynodon dactylon.*

Variety denomination: The new *Cynodon* bermudagrass is denominated '12-TG-101'.

BACKGROUND

The present invention relates to a new and distinct cultivar of hybrid *Cynodon* bermudagrass botanically known as *Cynodon transvaalensis* x *Cynodon dactylon* and has been given the varietal name '12-TG-101.' The new *Cynodon* '12-TG-101' was collected as a mutant and then evaluated as a product of a breeding program conducted by the inventor in Tifton, Ga. The objective of the bermudagrass breeding program is to create new plant cultivars with improved commercial qualities. This cultivar is commercially important for its superior turfgrass uniformity, very dark green leaf color, high putting green speeds, and other qualities, which are enumerated herein.

Pedigree and history: On Apr. 13, 2012, 155 putative somatic mutants derived from the original *Cynodon* 'Tifgreen' (Tifton 328) bermudagrass that had been planted on the putting greens 51 years prior were collected from a golf course at Fort Stewart in Georgia. 'Tifgreen' is an unpatented hybrid derived from a cross between *Cynodon. transvaalensis* x *Cynodon. dactylon* that has naturally and spontaneously produced somatic mutations since its creation in the 1950's and continues to do so today. Of the collected 'Tifgreen' mutants, '12-TG-101' was collected from the 13th green. Two identical, replicated field trials were established in 2013 and 2014 at a site in Tifton, Ga. where inflorescence, morphological, and turfgrass performance observations were recorded on these 155 putative somatic mutants for comparison with the bermudagrass cultivars 'Tifgreen', 'Tifdwarf' (unpatented), Champion™ ('Champion Dwarf' U.S. Plant Pat. No. 9,888P), MiniVerde® ('P18' U.S. Plant Pat. No. 12,084P2), and 'TifEagle' (U.S. Plant Pat. No. 11,163). Of the 155 mutants, '12-TG-101' was highly adapted to the management conditions of the research trials in Tifton, Ga., although they are notably of lower-intensity than what is possible on golf courses with more resources. '12-TG-101' was planted in 10 on-site golf course putting greens trials in the Southeastern United States from 2015 through 2019, under the restrictive terms of material transfer agreements, for evaluation under standard golf course maintenance protocols not possible at the original Tifton site.

Asexual reproduction of the new bermudagrass '12-TG-101' by vegetative terminal cuttings was established in a controlled environment in Tifton, Ga., and has continued since 2012. Observation of the 12-TG-101' progeny has shown that the unique features of this new bermudagrass are stable and reproduce true to type in successive generations.

SUMMARY

The cultivar '12-TG-101' has not been observed under all possible environmental conditions. The phenotype may vary somewhat with variations in environment and cultural practices such as temperature water and fertility levels, soil types, and light intensity, however, without any variance in genotype. The following traits have been repeatedly observed and have been determined to be the unique and distinguishing combination of characteristics of the new bermudagrass '12-TG-101'. In combination, these traits set '12-TG-101' apart from all other existing varieties of bermudagrass known to the inventors:

1. Superior turfgrass uniformity
2. Very dark green leaf color; and
3. Excellent putting green speeds.

'12-TG-101' has been compared to a number of grasses as discussed and set forth in Tables below.

In Tifton, Ga., ratings were taken monthly from April to October.

The new '12-TG-101' is a naturally occurring somatic mutant of 'Tifgreen'. Comparison to 'Tifgreen' (unpatented): '12-TG-101' has an inflorescence peduncle length (seed head height) that is shorter than 'Tifgreen'. '12-TG-101' has a lesser number of racemes per inflorescence (branches per flower) than 'Tifgreen'. The raceme length of '12-TG-101' is shorter than in 'Tifgreen'. '12-TG-101' has fewer florets per raceme than 'Tifgreen'. Leaf width of '12-TG-101' is narrower than that of 'Tifgreen'. Leaf length of '12-TG-101' is shorter than that of 'Tifgreen'. The terminal stolon internode lengths of '12-TG-101' are less than found on 'Tifgreen'. '12-TG-101' has a similar growth rate when planted as plugs, expressed as turf cover, as 'Tifgreen'. The genetic color observed for '12-TG-101' is higher (darker green) than for 'Tifgreen' as determined by digital image analysis in research trials in Tifton, Ga. '12-TG-101' has leaf color which most fits the Green Group 137B of The Royal Horticultural Society (R.H.S.) Colour Chart, 5th Edition, whereas that of 'Tifgreen' most fits the Green Group 146C.

Comparison to 'TifEagle' (U.S. Plant Pat. No. 11,163): '12-TG-101' has an inflorescence peduncle length (seed head height) that is similar to 'TifEagle'. '12-TG-101' has a similar number of racemes per inflorescence (branches per flower) as 'TifEagle'. The raceme length of '12-TG-101' is longer than in 'TifEagle'. '12-TG-101' has more florets per raceme than 'TifEagle'. Leaf width of '12-TG-101' is similar to that of 'TifEagle'. Leaf length of '12-TG-101' is similar to that of 'TifEagle'. The terminal stolon internode lengths of '12-TG-101' are longer than found on 'TifEagle'. '12-TG-101' has a faster growth rate when planted as plugs, expressed as turf cover, than 'TifEagle'. The genetic color observed for '12-TG-101' is higher (darker green) than for 'TifEagle' as determined by digital image analysis in research trials in Tifton, Ga., and darker green than 'TifEagle' across 10 golf course putting green performance trials according to visual ratings. '12-TG-101' and 'TifEagle' had the lowest canopy heights of all cultivars when left un-mowed for approximately 50 days during establishment in Tifton, Ga. Across the golf course putting green performance trials, '12-TG-101' was visually darker green and more uniform than 'TifEagle', but had the same green speeds as determined with a Stimpmeter. '12-TG-101' has leaf color which most fits the Green Group 137B of The Royal Horticultural Society (R.H.S.) Colour Chart, 5th Edition, whereas that of 'TifEagle' most fits the Green Group 146B.

Comparison to Champion™ (U.S. Plant Pat. No. 9,888 P): '12-TG-101' has an inflorescence peduncle length (seed head height) that is similar to Champion™. '12-TG-101' has a similar number of racemes per inflorescence (branches per flower) as Champion™. The raceme length of '12-TG-101' is similar to that of Champion™. '12-TG-101' has a similar number of florets per raceme as Champion™. Leaf width of '12-TG-101' is narrower than that of Champion™. Leaf length of '12-TG-101' is shorter than that of Champion™. The terminal stolon internode lengths of '12-TG-101' are similar to those found on Champion™. '12-TG-101' has a faster growth rate when planted as plugs, expressed as turf cover, than Champion™. The genetic color observed for '12-TG-101' is higher (darker green) than for Champion™ as determined by digital image analysis in research trials in Tifton, Ga. '12-TG-101' has leaf color which most fits the Green Group 137B of The Royal Horticultural Society (R.H.S.) Colour Chart, 5th Edition, whereas that of Champion™ most fits the Green Group 146B.

Comparison to MiniVerde® (U.S. Plant Pat. No. 12,084 P2): '12-TG-101' has an inflorescence peduncle length (seed head height) that is similar to MiniVerde®. '12-TG-101' has a similar number of racemes per inflorescence (branches per flower) as MiniVerde®. The raceme length of '12-TG-101' is longer than in MiniVerde®. '12-TG-101' has more florets per raceme than MiniVerde®. Leaf width of '12-TG-101' is similar to that of MiniVerde®. Leaf length of '12-TG-101' is very similar to that of MiniVerde®. The terminal stolon internode lengths of '12-TG-101' are longer than found on MiniVerde®. '12-TG-101' has a faster growth rate when planted as plugs, expressed as turf cover, than MiniVerde®. The genetic color observed for '12-TG-101' is higher (darker green) than for MiniVerde® as determined by digital image analysis in research trials in Tifton, Ga. '12-TG-101' has leaf color which most fits the Green Group 137B of The Royal Horticultural Society (R.H.S.) Colour Chart, 5th Edition, whereas that of MiniVerde® most fits the Green Group 146A.

TABLE 1

Summary of inflorescence morphology of '12-TG-101' bermudagrass compared to other bermudagrass genotypes measured during 2015, 2016, and 2017 in Tifton, GA[1].

| Genotype | Year of release | Inflorescence peduncle length mm | Racemes per inflorescence number | Raceme length mm | Florets per raceme number |
|---|---|---|---|---|---|
| '12-TG-101' | 2021 | 14 bc[2] | 2.3 b | 10 c | 7.6 b |
| 'TifEagle' | 1997 | 14 bc | 2.2 b | 8 d | 5.0 c |
| Mini Verde ®[3] | 1992 | 12 c | 2.2 b | 9 d | 5.6 c |
| Champion ™[4] | 1987 | 15 b | 2.5 b | 11 bc | 8.4 c |
| 'Tifdwarf' | 1964 | 16 b | 2.4 b | 12 b | 8.5 b |
| 'Tifgreen' | 1956 | 24 a | 2.9 a | 15 a | 11.0 a |

[1]Field trial planted during 2013.
[2]Means within columns followed by the same letter are not significantly different at K = 100 (approximates P = 0.05) according to the Waller-Duncan LSD.
[3]Inflorescences not present during 2015 and 2016.
[4]Inflorescences not present during 2015.

TABLE 2

Summary of vegetative plant morphology of '12-TG-101' bermudagrass compared to other bermudagrass genotypes measured during 2013 and 2014 in Tifton, GA[1].

| Genotype | Year of release | Leaf width[2] mm | Leaf length[3] mm | Stolon internode length[4] mm | Turf cover[5] % green | Turf color[6] DGCI | Turf canopy height[7] cm |
|---|---|---|---|---|---|---|---|
| '12-TG-101' | 2021 | 1.9 ab[8] | 10 de | 19 b | 35 a | 0.75 a | 1.1 d |

TABLE 2-continued

Summary of vegetative plant morphology of '12-TG-101' bermudagrass compared to other bermudagrass genotypes measured during 2013 and 2014 in Tifton, GA[1].

| Genotype | Year of release | Leaf width[2] mm | Leaf length[3] mm | Stolon inter-node length[4] mm | Turf cover[5] % green | Turf color[6] DGCI | Turf canopy height[7] cm |
|---|---|---|---|---|---|---|---|
| 'TifEagle' | 1997 | 1.8 bc | 9 e | 10 d | 9 b | 0.68 cd | 1.4 cd |
| Mini-Verde ® | 1992 | 1.8 bc | 14 cd | 15 c | 14 b | 0.69 bc | 1.7 c |
| Champ-ion ™ | 1987 | 1.7 c | 20 b | 16 bc | 16 b | 0.64 d | 2.6 b |
| 'Tifdwarf' | 1964 | 2.0 a | 16 c | 11 d | 14 b | 0.72 ab | 2.6 b |
| 'Tifgreen' | 1956 | 1.7 c | 30 a | 26 a | 31 a | 0.65 cd | 4.1 a |

[1]Field trials planted during 2013 and 2014.
[2]Leaf widths were measured on the first fully expanded leaf of a mature phytomer in the turf canopy.
[3]Leaf lengths were measured on the first fully expanded leaf of a mature phytomer in the turf canopy.
[4]Stolon internode lengths were measured between the 3rd and 4th node of an apical meristem.
[5]Turf cover was determined by analyzing digital images taken in an enclosed photo box with a constant light source using SigmaScan Pro to measure the percentage of green pixels (0-100%) according to procedures developed by Richardson et al. (2001) in each plot 37 and 36 days after planting the 2013 and 2014 field trials, respectively.
[6]Turf color was determined by analyzing digital images taken in an enclosed photo box with a constant light source using SigmaScan Pro to measure the hue, saturation, and brightness and then calculate the dark green color index according to procedures developed by Karcher and Richardson (2003) in each plot 37 and 36 days after planting the 2013 and 2014 field trials, respectively.
[7]Turf canopy heights were measured from the ground to the top of the highest un-mowed leaves in each plot 49 and 50 days after planting the 2013 and 2014 fields trials, respectively.
[8]Means within columns followed by the same letter are not significantly different at K = 100 (approximates P = 0.05) according to the Waller-Duncan LSD.

TABLE 3

Summary of putting green performance of '12-TG-101' bermudagrass compared to 'TifEagle' bermudagrass measured between 2015-2021 on 10 golf courses in the Southeastern United States[1].

| Genotype | Year of release | Turf color[2] visual rating | Turf uniformity[3] visual rating | Green speed[4] m |
|---|---|---|---|---|
| '12-TG-101' | 2021 | 7.6 a | 7.6 a[5] | 2.88 a |
| 'TifEagle' | 1997 | 6.4 b | 6.9 b | 2.80 a |

[1]Field trials planted between 2015-2019 at 10 different golf courses in the Southeastern United States
[2]Turf color was visually rated on a 1 to 9 scale with 1 = yellow, 6 = acceptable, and 9 = dark green.
[3]Turf uniformity was visually rated on a 1 to 9 scale with 1 = least, 6 = acceptable, and 9 = most. Putting green surface leaf density, leaf width, leaf canopy distribution, leaf orientation, leaf mowing quality, and weed encroachment were all taken into consideration for the comprehensive turf uniformity visual rating.
[4]Green speeds were determined by measuring the distance golfballs rolled when released from an inclined plane called a Stimpmeter (United States Golf Association, 1979).
[5]Least squares means within columns followed by the same letter are not significantly different according to the Tukey-Kramer test ($P < 0.05$).

The foregoing and other objects, features, and advantages of the invention will become more apparent from the following detailed description, which proceeds with reference to the accompanying figures.

BRIEF DESCRIPTION OF THE DRAWINGS

The accompanying colored photographic illustrations show the overall appearance and distinct characteristics of the new cultivar of the new *Cynodon* bermudagrass named '12-TG-101' showing the colors as true as possible. Colors in the photographs may differ slightly from the color values cited in the detailed botanical description, which accurately describes the colors of the new '12-TG-101'.

DETAILED BOTANICAL DESCRIPTION

Figure 1:
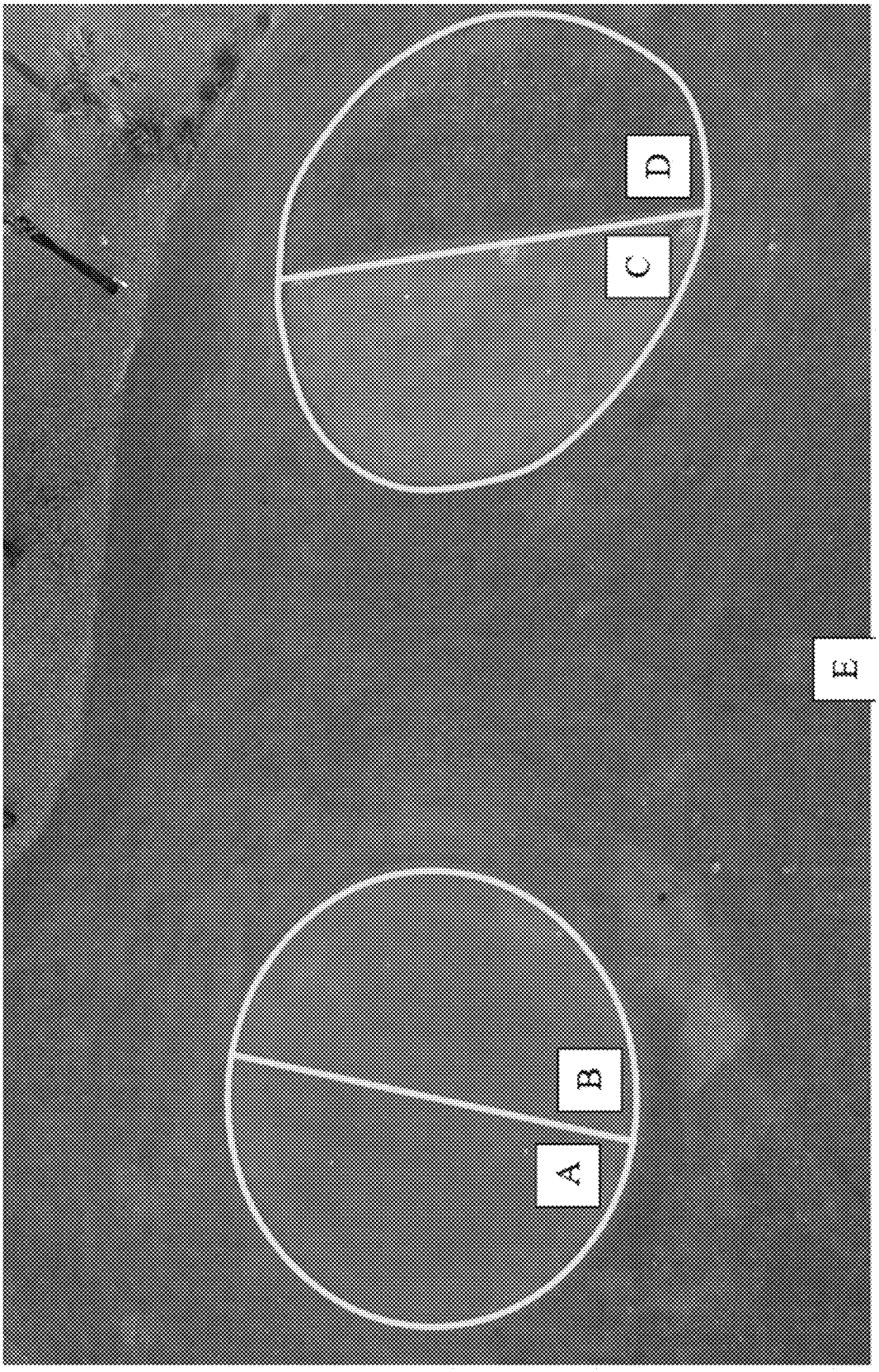
FIG. 1 is a photograph of five grass plots: '12-TG-101' (A), 'TifEagle' (B), and Mach 1® (registered trademark for 'Ace Award', U.S. Plant Pat. No. 31,139) (C) golf putting green plots mowed at 0.254 cm (0.100 in) alongside bermudagrass cultivars '11-T-56' (D) and TifGrand® ('ST-5' U.S. Plant Pat. No. 21,017) (E) plots mowed at 0.9525 cm (0.375 in). The photographs were taken of the plots at a golf course in Naples, Fla. on Mar. 13, 2021, after a 5-day dry-down in late February 2021. The trial was planted on Sep. 18, 2019.

The following observations, measurements, and values describe '12-TG-101' plants grown in Tifton, Ga. The following traits have been consistently observed and, to the best knowledge of the inventors, their combination forms the unique characteristics of the new variety '12-TG-101.' During the growing of the plants, typical day temperatures in Tifton, Ga. ranged from 69° F. to 99° F., and typical night temperatures ranged from 47° F. to 70° F.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by the Royal Horticultural Society, London, England in 2007, except where general terms of ordinary dictionary significance are used. '12-TG-101' has leaf color which most fits the Green Group 137B.

Botanical classification: *Cynodon* hybrid (Bermudagrass hybrid).

Commercial classification: Turfgrass.

Parentage: Somatic mutant of 'Tifgreen' (*Cynodon transvaalensis* x *Cynodon dactylon*).

Propagation type: '12-TG-101' is a triploid hybrid, which rarely produces seed or pollen, despite the fact that it produces more seed heads than some varieties. It is vegetatively propagated, ordinarily by sprigs or sod.

Inflorescence and racemes: '12-TG-101' has an inflorescence peduncle color of RHS 145A and length (seed head height) of about 14 mm, which is shorter than 'Tifgreen', but similar to 'TifEagle', MiniVerde®, Champion™, and 'Tifdwarf' (Table 1). '12-TG-101' has about 2.3 racemes per inflorescence (branches per flower), which is similar in number as 'TifEagle', MiniVerde®, Champion™, and 'Tifdwarf', but less than found for 'Tifgreen' (Table 1). The raceme length of '12-TG-101' is about 10 mm, which is similar to that of Champion™, shorter than in 'Tifdwarf' and 'Tifgreen', but longer than those of 'TifEagle' and MiniVerde® (Table 1). '12-TG-101' has about 7.5 florets per raceme, which is fewer than 'Tifgreen', more than 'TifEagle' and MiniVerde®, and a similar number to Champion™ and 'Tifdwarf' (Table 1). The sizes and/or R.H.S. colors for the following parts of the inflorescence were also measured: floret (145C, about 2.446 mm), palea (146D, about 2.378 mm), lemma (fertile, 145D, about 2.176 mm), and glume (upper, 145C and about 1.551 mm, and lower, 145C and about 1.313 mm).

Leaf: The leaf width of '12-TG-101' is about 1.9 mm, similar to, 'TifEagle', MiniVerde®, and 'Tifdwarf, but broader than those of Champion™ and 'Tifgreen' (Table 2). '12-TG-101' has a leaf length of about 10 mm, which is similar compared to 'TifEagle' and MiniVerde®, but shorter than observed in Champion™, 'Tifdwarf', and 'Tifgreen' (Table 2). The genetic leaf color observed for '12-TG-101' most fits the Green Group 137B and is higher (darker green) than for all cultivars except 'Tifdwarf' as determined by digital image analysis in research trials in Tifton, Ga. (Table 2), and darker green than 'TifEagle' across 10 golf course putting green performance trials according to visual ratings (Table 3). The very dark green leaf of '12-TG-101' distinguishes it from other ultradwarf cultivars, including 'TifEagle', MiniVerde®, and Champion™. The surface texture of the upper and lower leaf surfaces is smooth.

Stolons, collar region, and growth rate: The terminal stolon internode lengths of '12-TG-101' are about 19 mm, which are similar to those of Champion™, but less than found on 'Tifgreen' and longer than those of 'TifEagle', MiniVerde®, and 'Tifdwarf' (Table 2). The stolons have a R.H.S. color closest to 145C. '12-TG-101' has a faster growth rate when planted as plugs, expressed as turf cover, than all compared cultivars other than 'Tifgreen' (Table 2). In the collar region, the ligule has a R.H.S. color of 157A, and the sheath has a color of 145B and a size of about 4.427 mm. The collar type is continuous and constricted at midrib, with a R.H.S. color of 145D and a length of about 0.21 mm. The ligule type is hairy, and auricles are absent.

Turf features: '12-TG-101' has a turf canopy heigh of about 1.1 cm, which along with 'TifEagle' had the lowest canopy heights of all cultivars when left un-mowed for approximately 50 days during establishment in Tifton, Ga. (Table 2). '12-TG-101' had a turf cover of about 35%, which was greater than the other cultivars. Across the golf course putting green performance trials, '12-TG-101' was visually darker green and more uniform than 'TifEagle', with a turf color visual rating of 7.6 and turf uniformity visual rating of 7.6, but had similar green speeds as 'TifEagle', at about 2.88 m as determined with a Stimpmeter (Table 3).

Figure 2:
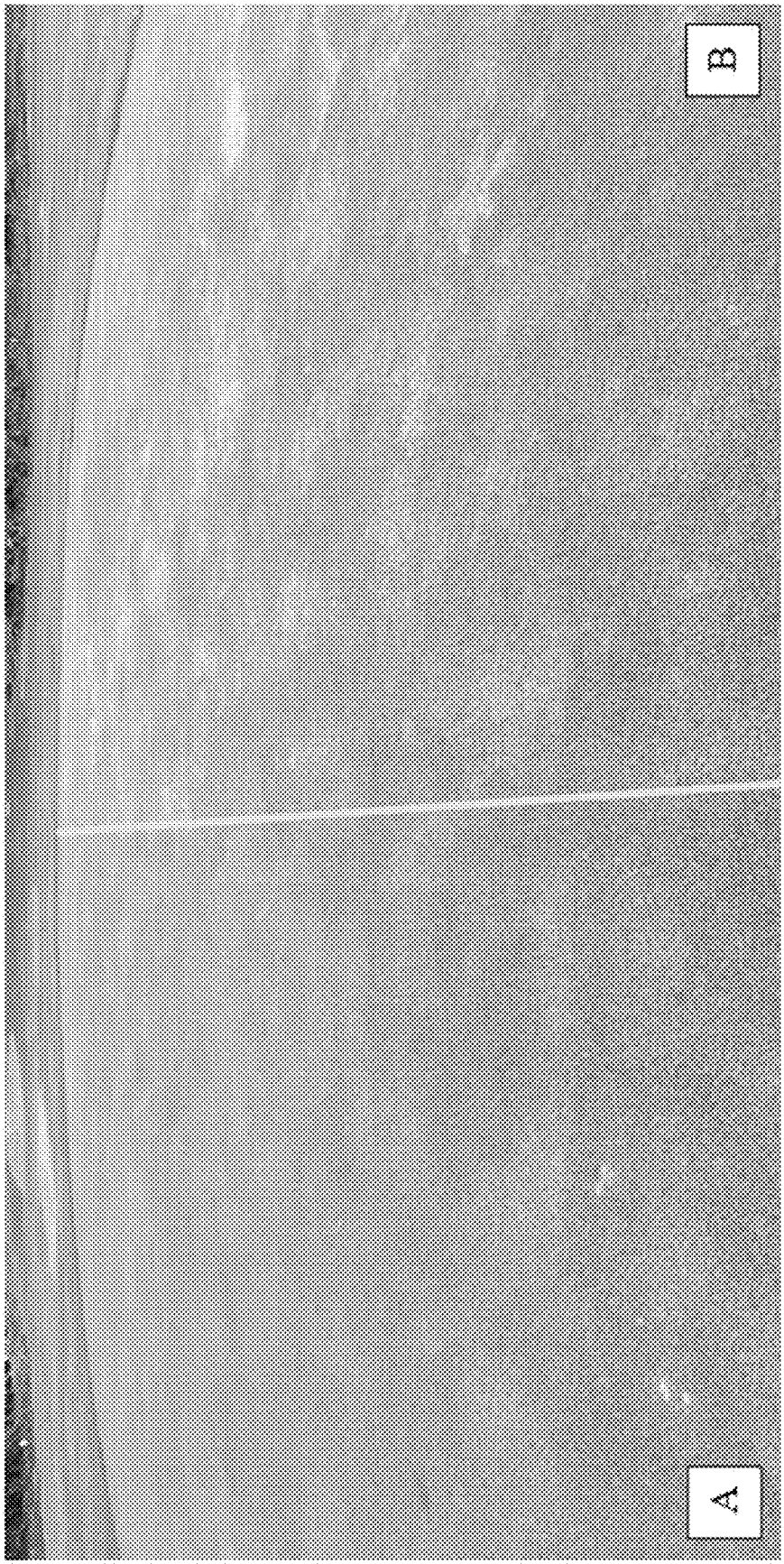
FIG. 2 is a photograph of different genotypic responses to mower scalping on adjacent golf greens plots of '12-TG-101' (A) and 'TifEagle' (B) mowed at 0.3175 cm (0.125 in) at a golf course in Naples, Fla., on Jul. 1, 2021, after a 2-month sustained period of lower agronomic maintenance intensity. The trial was planted on Sep. 18, 2019.
Figure 3:
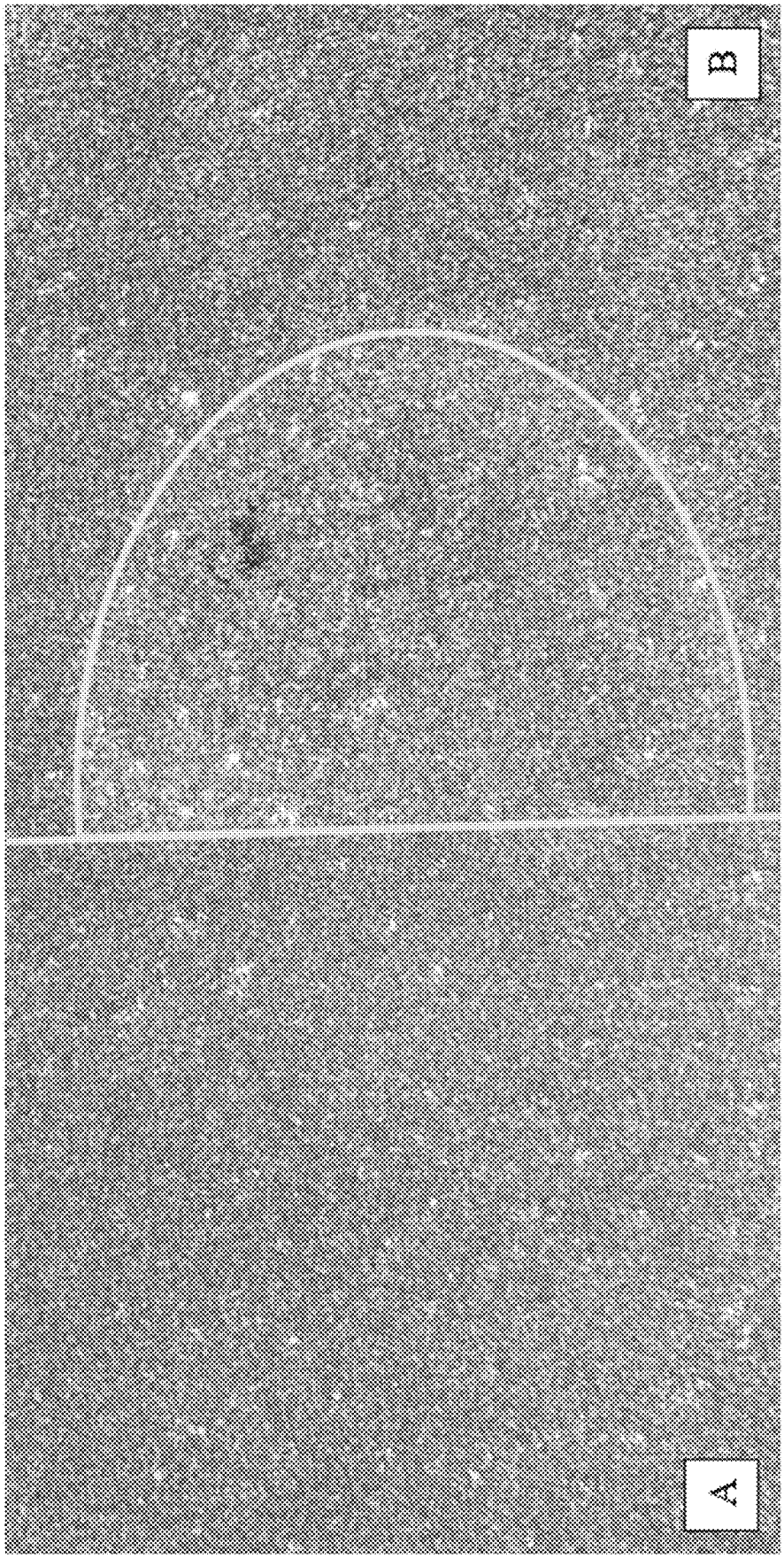
FIG. 3 is a photograph of different genetic responses to a root disease caused by *Gaeumannomyces graminis* on adjacent plots of '12-TG-101' (A) and Mach 1® (B) at a golf course in Atlanta, Ga., on Jun. 9, 2021, after hollow-core aeration in late May 2021. The trial was planted on May 1, 2019.
Figure 5:
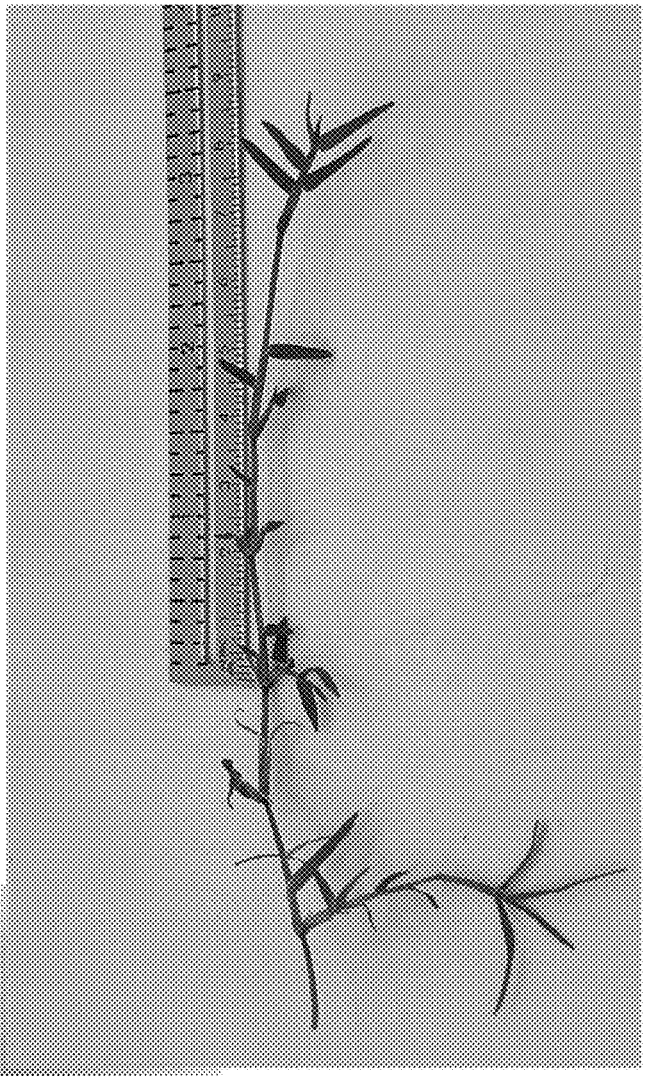
FIG. 5 is a close-up photograph of a stolon of '12-TG-101' illustrating the morphology and color of the leaves and stems.
Figure 4:
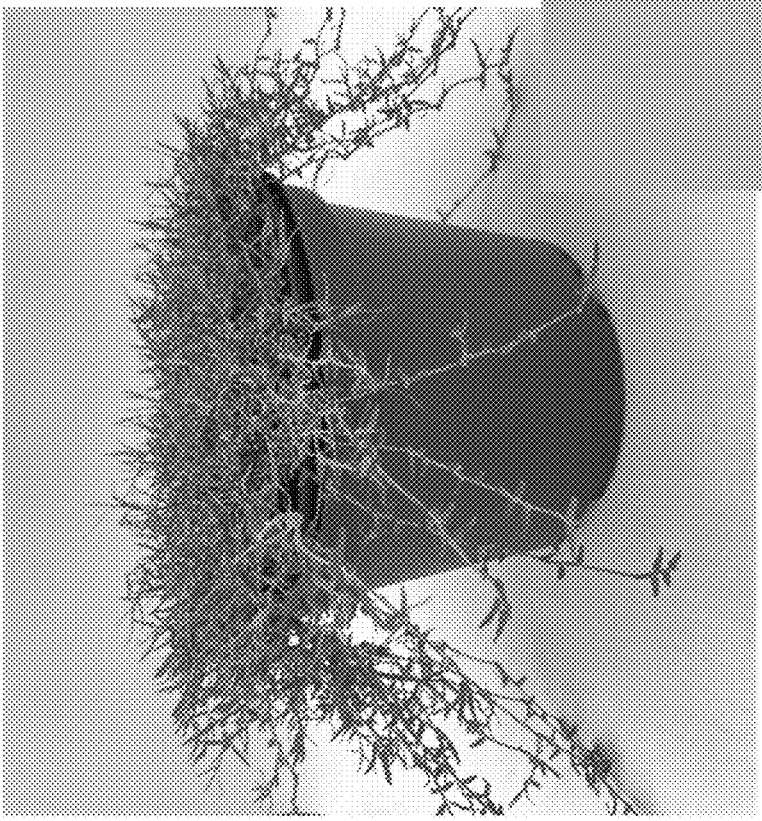
FIG. 4 is a photograph of a potted sample of '12-TG-101'. The '12-TG-101' sprig was planted in the pot on Jan. 7, 2022 and allowed to grow until the date of the photograph on Mar. 16, 2022.

Finally, '12-TG-101' handles mower scalping better than 'TifEagle'. This is shown in FIG. 2, where the scalping mower height for both cultivars was 0.125 inches. In general, scalping can occur in putting green grasses when thatch is not controlled, and according to anecdotal evidence, '12-TG-101' produces less thatch than other putting greens grasses.

In addition to the data provided in the Summary of the Invention, bermudagrass '12-TG-101' generally has superior turf uniformity to 'TifEagle' during, or immediately following, many environmental (e.g., drought and temperature fluctuations during the spring and fall) or mechanical (mower scalping, verticutting, and hollow core aeration) stresses. An underlying mechanism of the turf uniformity of '12-TG-101' may be its prostrate growth and recuperative potential as indicated by the morphological traits evaluated in Table 2.

We claim:

1. A new and distinct variety of the bermudagrass named '12-TG-101', substantially as illustrated and described herein.

* * * * *